(12) United States Patent
Miller et al.

(10) Patent No.: US 9,162,984 B2
(45) Date of Patent: Oct. 20, 2015

(54) SMALL-MOLECULE MODULATORS OF MELANIN EXPRESSION

(75) Inventors: Benjamin L. Miller, Penfield, NY (US); Brian R. McNaughton, Rochester, NY (US); Peter Gareiss, Rochester, NY (US); Glynis Scott, Rochester, NY (US)

(73) Assignee: University of Rochester, Rochester, NY (US)

( * ) Notice: Subject to any disclaimer, the term of this patent is extended or adjusted under 35 U.S.C. 154(b) by 1434 days.

(21) Appl. No.: 12/593,673

(22) PCT Filed: Mar. 28, 2008

(86) PCT No.: PCT/US2008/058716
§ 371 (c)(1),
(2), (4) Date: Mar. 11, 2010

(87) PCT Pub. No.: WO2008/121850
PCT Pub. Date: Oct. 9, 2008

(65) Prior Publication Data
US 2010/0233106 A1    Sep. 16, 2010

Related U.S. Application Data

(60) Provisional application No. 60/909,264, filed on Mar. 30, 2007.

(51) Int. Cl.
*A61K 8/49* (2006.01)
*C07D 215/54* (2006.01)
*A61K 31/47* (2006.01)
*C07D 211/14* (2006.01)
*C07D 261/18* (2006.01)
*C07D 307/68* (2006.01)
*C07D 405/06* (2006.01)

(52) U.S. Cl.
CPC ............ *C07D 215/54* (2013.01); *C07D 211/14* (2013.01); *C07D 261/18* (2013.01); *C07D 307/68* (2013.01); *C07D 405/06* (2013.01)

(58) Field of Classification Search
CPC .................................................. C07D 215/54
See application file for complete search history.

(56) References Cited

U.S. PATENT DOCUMENTS

| 2004/0067209 A1 | 4/2004 | Brown et al. |
| 2004/0265252 A1 | 12/2004 | Orlow et al. |
| 2005/0142078 A1 | 6/2005 | Dorr et al. |
| 2005/0202001 A1 | 9/2005 | Koo et al. |
| 2006/0188953 A1 | 8/2006 | Orlow et al. |

FOREIGN PATENT DOCUMENTS

| WO | 99/56740 A1 | 11/1999 |
| WO | 2004/069792 A2 | 8/2004 |

OTHER PUBLICATIONS

Perrier et al. Liquid-Phase Synthesis with Solid-Phase Workup: Application to Multistep and Combinatorial Syntheses. J. Org. Chem. 64, pp. 2110-13 (1999).*
Voltrova et al. Synthesis of biologically interesting 1-substituted 5- and 8-aminoquinoline-3-carboxylic acid derivatives. Afinidad 58, 491, pp. 61-68 (2001).*
Ukhov et al. 2. Naphthypyridines. 15. 2-Styrylquinoline-3-carboxylic acid amides and their cyclization into substituted 3-aryl-1-oxo-1,2,3,4-tetrahydrobenzo[b]-1,6-naphthyridines. Khimiya Geterotsiklicheskikh Soedinenii (1), pp. 92-94 (1992) (abstract).*
Jung et al. "Gem-Dialkyl Effect in the Intramolecular Dies-Alder Reaction of 2-Furfural Methyl Fumarates: The Reactive Rotamer Effect, Enthalpic Basis for Acceleration, and Evidence for a Polar Transition State," J. Am. Chem. Soc. 113:224-232 (1992).
White et al. "Base-Catalyzed Hydrogen-Tritium Exchange Rates of Omega-Tritium-Substituted Picolines and methylquinolines," J. Org. Chem. 34:2756-2759 (1969).
International Search Report for PCT/US2008/058716, Mar. 28, 2008.
Jung et al., "Identification of the F1F0 Mitochondrial ATPase as a Target for Modulating Skin Pigmentation by Screening a Tagged Triazine Library in Zebrafish," Molecular BioSystems 1(1):85-92 (2005).
Komatsu et al., "Identification of Novel Pigmentation Modulators by Chemical Genetic Screening," J. Invest. Derm. 127:1585-1592 (2007).
McNaughton et al., "Identification of Novel Small Molecule Inducers of Melanin Production," Journal of Investigative Dermatology, vol. 127, Issue S1, S153 (Apr. 2007) (Abstract # 917).
D'Orazio et al., "Topical Drug Rescue Strategy and Skin Protection Based on the Role of Mc1r in UV-Induced Tanning," Nature 443(21):340-344 (2006).

* cited by examiner

*Primary Examiner* — Barbara P Badio
*Assistant Examiner* — Sara E Townsley
(74) *Attorney, Agent, or Firm* — LeClairRyan, a Professional Corporation

(57) ABSTRACT

The present invention relates to small molecule modulators of melanin expression and methods of making the small molecules. Also disclosed are methods of increasing pigmentation in a cell which involve providing compounds of the present invention and contacting a cell with the compounds under conditions effective to induce melanin expression in the cell, thereby increasing pigmentation. The present invention also relates to compositions containing compounds of the present invention and a carrier.

6 Claims, 4 Drawing Sheets

SMALL-MOLECULE MODULATORS OF MELANIN EXPRESSION

This application is a national stage application under 35 U.S.C. 371 of PCT/US2008/058716, filed Mar. 28, 2008, and claims the priority benefit of U.S. Provisional Patent Application Ser. No. 60/909,264, filed Mar. 30, 2007, which is hereby incorporated by reference in its entirety.

The subject matter of this application was made with support from the United States Government under NIH Grant No. T32 AR007472. The U.S. Government has certain rights.

FIELD OF THE INVENTION

The present invention relates to small-molecule modulators of melanin expression, compositions containing the compounds, and methods of using the compounds to induce melanin expression (i.e., in melanocytes) and increase skin pigmentation.

BACKGROUND OF THE INVENTION

Melanin is a complex biopolymer that is synthesized in organelles called melanosomes that are a unique feature of melanocytes. Melanocytes are cells that reside in the basal layer of the epidermis and transfer melanin to neighboring keratinocytes. In melanin synthesis, early oxidative steps in which phenolic and catecholic precursors are oxidized to orthoquinones occurs. Regulation of melanin production occurs at multiple points that primarily involve, but are not exclusive to, the regulation of tyrosinase, which is the key enzyme in melanin synthesis (Wang et al., "Tyrosinase Maturation Through the Mammalian Secretory Pathway: Bringing Color to Life," *Pigment Cell Res.* 19:3-18 (2006); Wang et al., "Regulation of Tyrosinase Trafficking and Processing by Presenilins: Partial Loss of Function by Familial Alzheimer's Disease Mutation," *Proc. Natl. Acad. Sci. USA* 103:353-8 (2006)). However, because over 100 genes are implicated in control of pigmentation, other regulatory targets are likely to exist.

Melanin is important for disease prevention, because it absorbs ultraviolet light in the UVB and UVA spectrum. This protects keratinocytes from the mutagenic effects of sunlight. In addition, melanin has a social function, because it determines skin and hair color. Cutaneous cancers such as squamous cell carcinoma and basal cell carcinoma are directly linked to exposure to ultraviolet irradiation, and it is widely accepted that people with light skin are at much higher risk to develop skin cancer due to a comparative lack of melanin compared with dark skinned individuals (Gallagher et al., "Adverse Effects of Ultraviolet Radiation: A Brief Review," *Prog. Biophys. Mol. Biol.* 92(1):119-31 (2006)).

Agents that increase melanin synthesis are of interest, because of their potential use as "natural sunscreens" that stimulate the skin's resident melanocytes to produce and transfer more melanin to epidermal keratinocytes, thus decreasing the incidence of skin cancer. There is a significant need to identify new compounds with improved ability to induce melanin production and transfer. The development of libraries of compounds that can be rapidly screened for their ability to modulate melanin production would facilitate drug discovery that could have a profound impact on the incidence of skin cancer.

The present invention is directed to overcoming these and other deficiencies in the art.

SUMMARY OF THE INVENTION

A first aspect of the present invention relates to a compound formed by a reaction of a carboxylic acid and an amine. The carboxylic acid is selected from

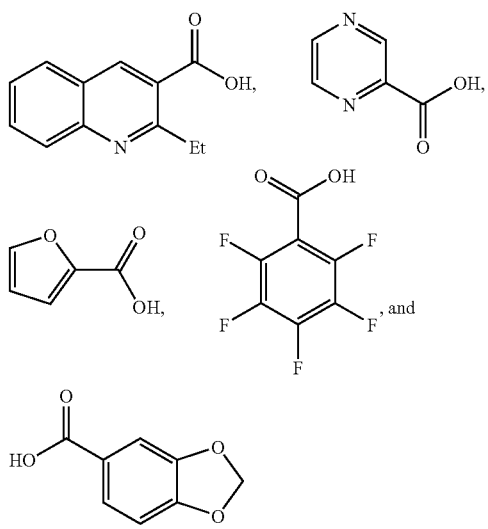

and the amine is selected from

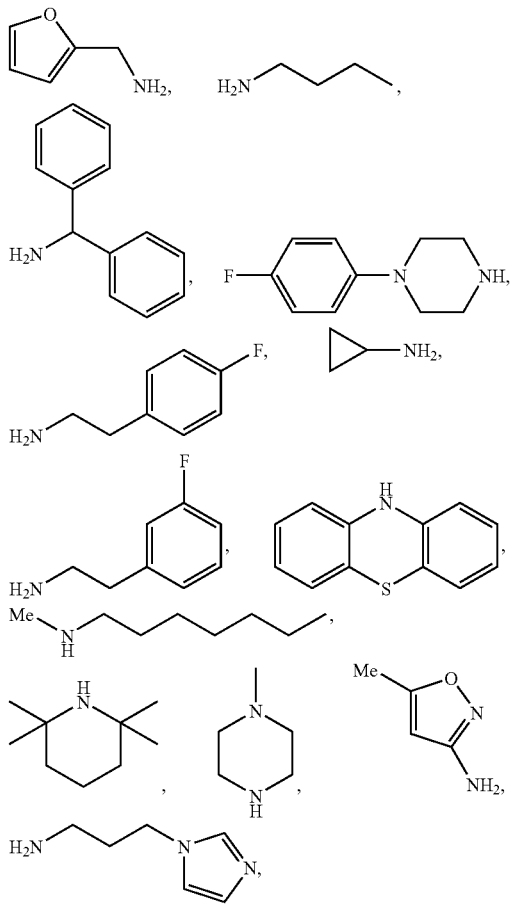

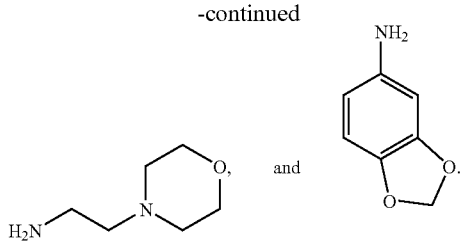

A second aspect of the present invention relates to a compound according to formula (I)

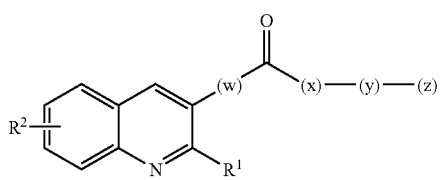

wherein,
R$^1$ is selected from H and straight or branched chain C$_1$ to C$_6$ hydrocarbon;
R$^2$ is selected from —O—R$^3$, —NH—R$^3$, and —S—R$^3$, where R$^3$ is selected from H, straight or branched chain C$_1$ to C$_6$ hydrocarbon, and alkoxyalkyl;
W is a straight or branched chain C$_1$ to C$_6$ hydrocarbon, —(CH$_2$)$_p$NH—, or —(CH$_2$)$_p$N(CH$_3$)—, where p is an integer from 0 to 3;
X is selected from (CH$_2$)$_n$, O, —(CH$_2$)$_q$NH—, or —(CH$_2$)$_q$N(CH$_3$)—, where n is an integer from 0 to 8 and q is an integer from 0 to 3;
Y is selected from (CH$_2$)$_m$, where m is an integer from 0 to 3; and
Z is selected from

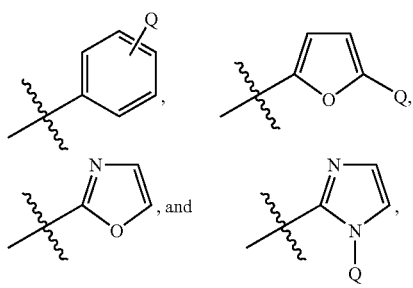

where Q is selected from H and halogen.

A third aspect of the present invention relates to a compound according to formula (II)

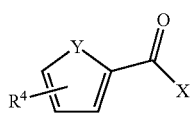

wherein,
R$^4$ is selected from H and straight or branched chain C$_1$ to C$_6$ hydrocarbon;

Y is selected from O, N—R$^5$, and S—R$^5$, where R$^5$ is selected from H and straight or branched chain C$_1$ to C$_6$ hydrocarbon;
X is selected from R$^6$, O—R$^6$, NH—R$^6$, NR$^6$$_2$,

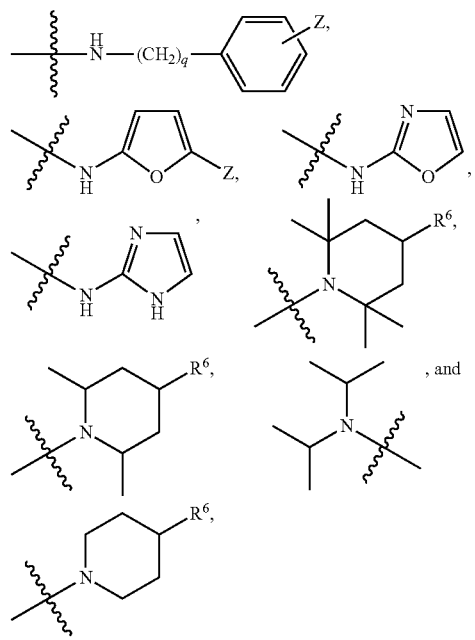

wherein each R$^6$ is independently selected from H, straight or branched chain C$_1$ to C$_6$ hydrocarbon, and halogen; q is an integer from 0 to 5; and Z is selected from H, halogen, and C$_1$ to C$_3$ hydrocarbon.

A fourth aspect of the present invention relates to a method of increasing pigmentation in a cell. This method involves providing a compound according to the first, second, or third aspects of the present invention, or a combination thereof, and contacting a cell with the compound under conditions effective to induce melanin expression in the cell, thereby increasing pigmentation.

A fifth aspect of the present invention relates to a composition containing a carrier, and a compound according to the first, second, or third aspects of the present invention, or combinations thereof.

A sixth aspect of the present invention relates to a method of increasing skin pigmentation. This method involves applying a composition according to the fifth aspect of the present invention to skin on a subject in a manner and quantity effective to induce melanin production in contacted skin cells, thereby increasing skin pigmentation within a treated area of the skin.

A seventh aspect of the present invention relates to a method of making an amide compound according to the first, second, or third aspects of the present invention. This method involves providing a carboxylic acid and reacting the carboxylic acid with an amine under conditions effective to make an amide compound according to the first, second, or third aspects of the present invention.

An eighth aspect of the present invention relates to a method of making a compound according to formula (I) where X is oxygen. This method involves providing an isoquinoline carboxylic acid according to formula (III)

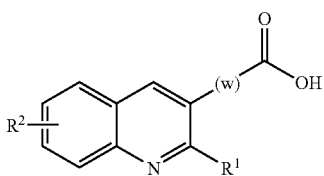

(III)

wherein $R^1$, $R^2$, and W are defined as in formula (I); and reacting the isoquinoline carboxylic acid of formula (III) with an alcohol of formula (IV)

HO-(y)-(z)     (IV), wherein Y and Z are defined as in formula (I). The reaction is carried out under conditions effective to make a compound according to formula (I) where X is oxygen.

A ninth aspect of the present invention relates to a method of making a compound of formula (I) where X is $(CH_2)_n$. This method involves providing an isoquinoline carboxylic acid according to formula (III) above. The isoquinoline carboxylic acid according to formula (III) is converted to a Weinreb amide via treatment with carbonyl diimidazole followed by N,O-Dimethylhydroxylamine. The resulting Weinreb amide is then treated with an alkyl Grignard reagent of formula (V)

(Z)—(Y)—$(CH_2)_n$—MgBr,     (V)

where Y is selected from $(CH_2)_m$, where m is an integer from 0 to 3, Z is selected from

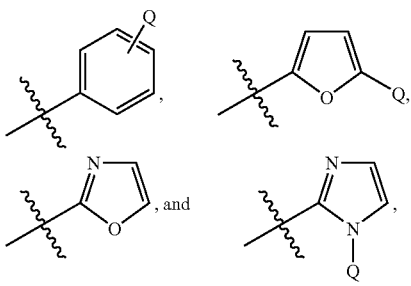

and Q is selected from H and halogen. These steps are carried out under conditions effective to make a compound of formula (I) where X is $(CH_2)_n$.

A tenth aspect of the present invention relates to a method of making a compound of formula (II) having an ester linkage in the sidechain. This method involves providing a carboxylic acid according to formula (VII)

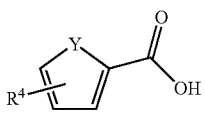

(VII)

where $R^4$ and Y are defined as in formula II, and reacting the carboxylic acid of formula (VII) with an alcohol of formula (VIII)

$R^6$—OH     (VIII)

where $R^6$ is a straight or branched chain $C_1$ to $C_6$ hydrocarbon, under conditions effective to make the compound of formula (II).

An eleventh aspect of the present invention relates to a method of making a compound of formula (II) where X is $R^6$, a straight or branched chain $C_1$ to $C_6$ hydrocarbon. This method involves providing a carboxylic acid according to formula (VII)

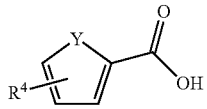

(VII)

where $R^4$ and Y are defined as in formula (II), and converting the carboxylic acid to a Weinreb amide via treatment with carbonyl diimidazole followed by N,O-Dimethylhydroxylamine. The Weinreb amide is treated with an alkyl Grignard reagent, $(R^6)$—MgBr under conditions effective to make a compound of formula (II) where X is a hydrocarbon as defined above.

A twelfth aspect of the present invention is directed to a method of making an ester compound according to formula (II). This method involves providing an acyl halide according to formula (IX)

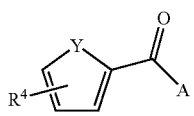

(IX)

where A is halogen and $R^4$ and Y are as defined in formula (II), and reacting the acyl halide with an alcohol of formula (VIII)

$R^6$—OH     (VIII)

where $R^6$ is a straight or branched chain $C_1$ to $C_6$ hydrocarbon, under conditions effective to make the compound of formula (II).

Several compounds of the present invention have been shown to induce increased melanin production in treated melanocytes, and importantly this occurs without concomitant increased cellular proliferation by the treated melanocytes. As a consequence, the compounds of the present invention, and compounds derived therefrom, are expected to be useful in topical compositions for the treatment of skin to induce increased skin pigmentation.

DETAILED DESCRIPTION OF THE INVENTION

Figure 1:
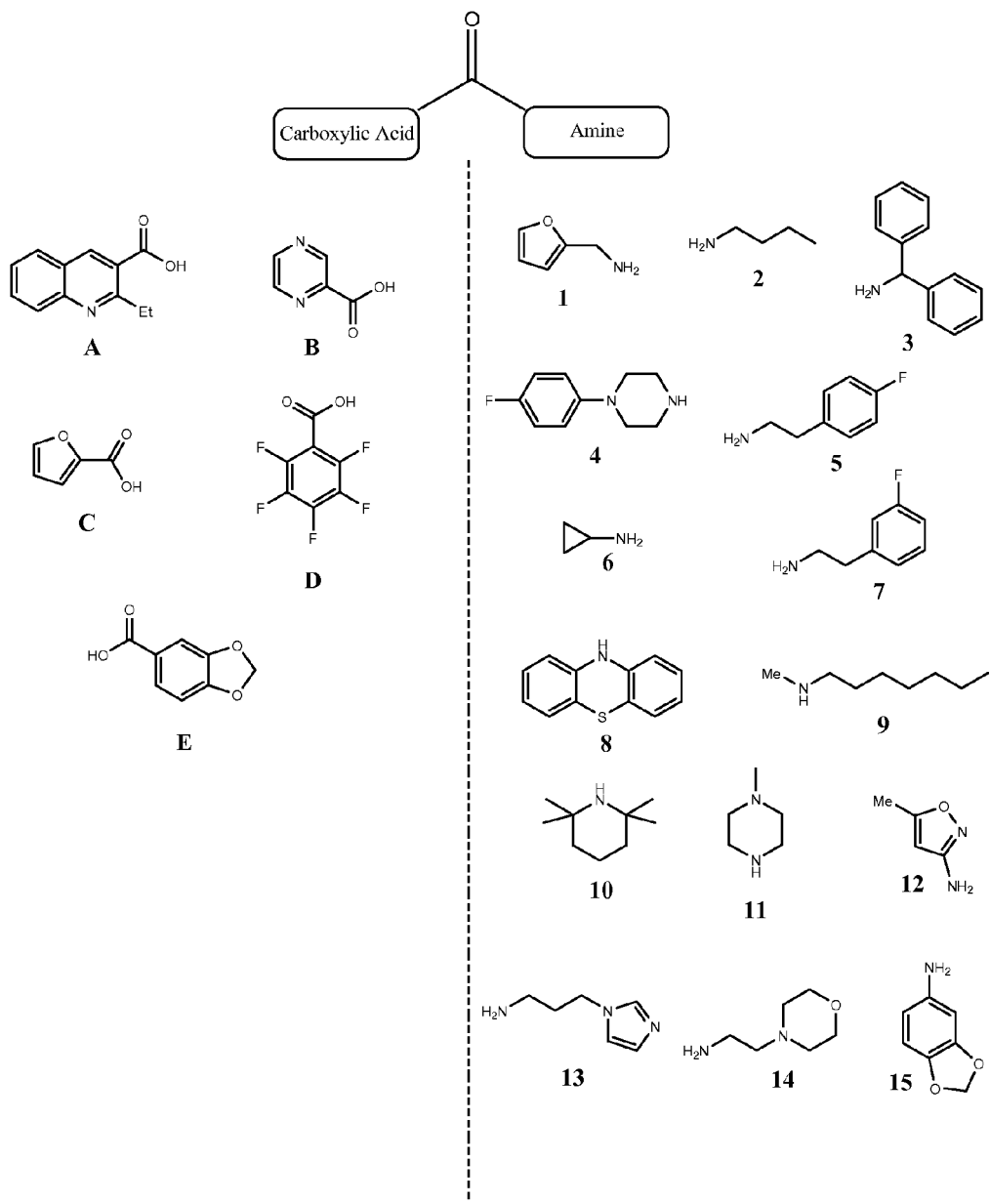
FIG. 1 is a schematic illustration showing how a small combinatorial library of 75 low molecular weight (<500 AMU), structurally diverse heterocyclic compounds was synthesized.

The present invention relates to the identification of novel compounds that are capable of inducing melanocyte expression of melanin, and therefore are capable of use for increasing skin pigmentation (i.e., in keratinocytes). The compounds, compositions suitable for administering them, and their methods of use are described herein.

A first aspect of the present invention relates to a compound formed by a reaction of a carboxylic acid and an amine. The carboxylic acid is selected from

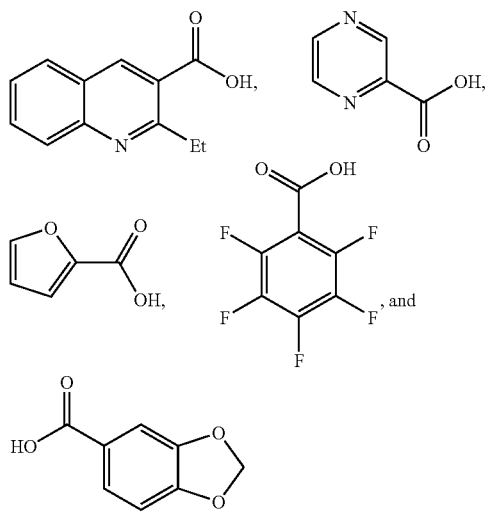

and the amine is selected from

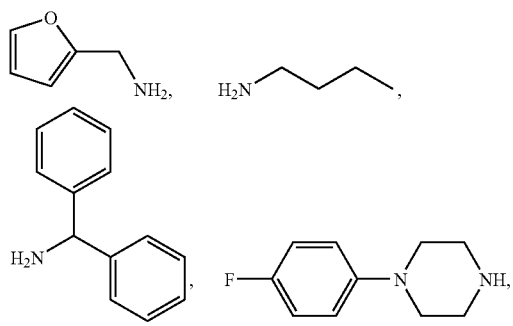

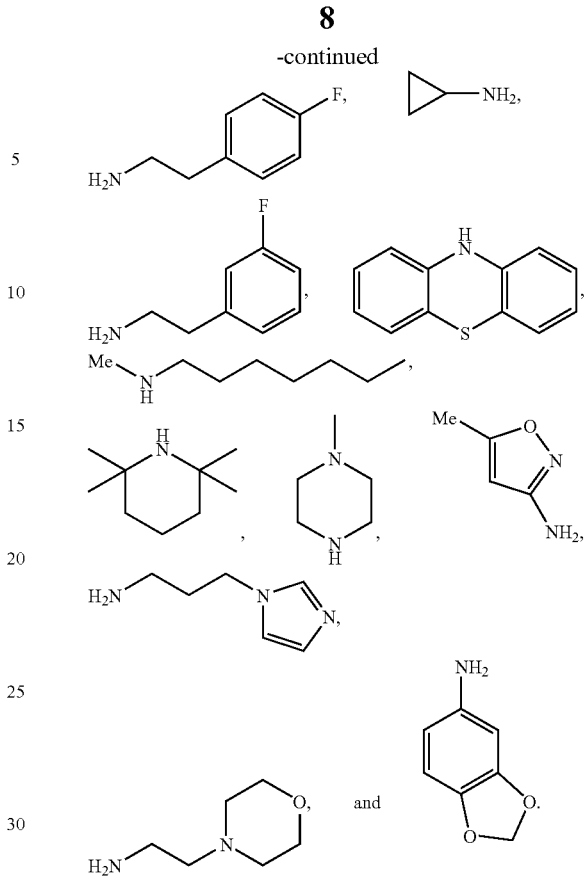

The reaction of a carboxylic acid with an amine to form an amide is a common reaction known by those of ordinary skill in the art. Typically, the carboxylic acid is activated by reacting it with an activating agent. For example, the carboxylic acid may be transformed to an acid chloride by treatment with oxalyl chloride or another similar agent. The acid chloride is then reacted with the amine in the presence of a base to form the amide.

Compounds of the present invention formed by a reaction of a carboxylic acid and an amine may have any combination of a carboxylic acid selected from the above "library" of carboxylic acids and an amine selected from the above "library" of amines. Examples of particular compounds of the present invention formed by a reaction of a carboxylic acid and an amine are set forth in Table 1.

TABLE 1

Compounds Formed by a Reaction of a Carboxylic Acid and an Amine

| Compound | Name | Structure |
|---|---|---|
| A5 | N-(4-fluorophenethyl)-2-ethylquinoline-3-carboxamide | 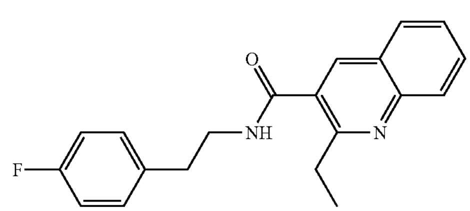 [SMILES: CCc1nc2ccccc2cc1C(=O)NCCc1ccc(F)cc1] |

TABLE 1-continued

Compounds Formed by a Reaction of a Carboxylic Acid and an Amine

| Compound | Name | Structure |
|---|---|---|
| A7 | N-(3-fluorophenethyl)-2-ethylquinoline-3-carboxamide | 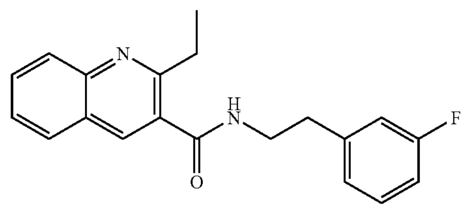 [SMILES: CCc1nc2ccccc2cc1C(=O)NCCc1cccc(F)c1] |
| C1 | N-((furan-2-yl)methyl)furan-2-carboxamide | 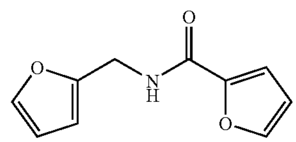 [SMILES: O=C(NCc1ccco1)c1ccco1] |
| C2 | N-butylfuran-2-carboxamide | 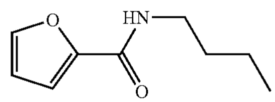 |
| C5 | N-(4-fluorophenethyl)furan-2-carboxamide | 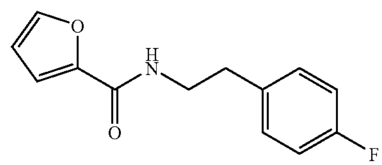 [SMILES: O=C(NCCc1ccc(F)cc1)c1ccco1] |
| C7 | N-(3-fluorophenethyl)furan-2-carboxamide | 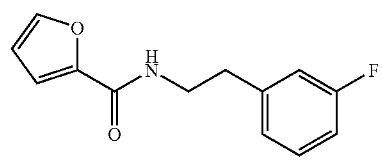 [SMILES: O=C(NCCc1cccc(F)c1)c1ccco1] |
| C10 | (furan-2-yl)(2,2,6,6-tetramethylpiperidin-1-yl)methanone | 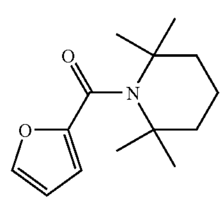 [SMILES: CC1(C)CCCC(C)(C)N1C(=O)c1ccco1] |
| D10 | (2,2,6,6-tetramethylpiperidin-1-yl)(perfluorophenyl)methanone | 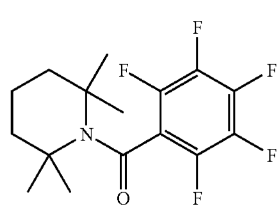 [SMILES: CC1(C)CCCC(C)(C)N1C(=O)c1c(F)c(F)c(F)c(F)c1F] |
| D12 | 2,3,4,5,6-pentafluoro-N-(5-methylisoxazol-3-yl)benzamide | 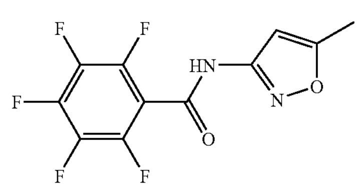 [SMILES: Cc1cc(NC(=O)c2c(F)c(F)c(F)c(F)c2F)no1] |

TABLE 1-continued

Compounds Formed by a Reaction of a Carboxylic Acid and an Amine

| Compound | Name | Structure |
|---|---|---|
| E4 | (benzo[d][1,3]dioxol-5-yl)(4-(4-fluorophenyl)piperazin-1-yl)methanone | 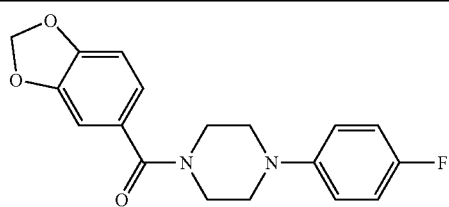 |

By virtue of the activity of the quinoline compounds identified in Table 1 above, the present invention also relates to compounds according to formula (I)

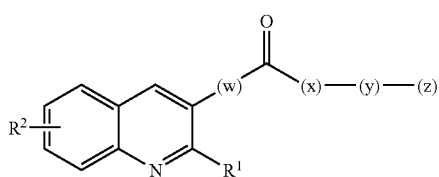

wherein,
R$^1$ is selected from H and straight or branched chain C$_1$ to C$_6$ hydrocarbon, preferably hydrogen, methyl, ethyl, propyl, isopropyl, or t-butyl;
R$^2$ is selected from —O—R$^3$, —NH—R$^3$, and —S—R$^3$, where R$^3$ is selected from H, straight or branched chain C$_1$ to C$_6$ hydrocarbon, and alkoxyalkyl, preferably methoxy, ethoxy, propoxy, methoxyethyl, N-methyl amino, N-ethyl amino, N-propyl amino, methylthio, ethylthio, or propylthio;
W is optional and can be a straight or branched chain C$_1$ to C$_6$ hydrocarbon, —(CH$_2$)$_p$NH—, or —(CH$_2$)$_p$N(CH$_3$)—, where p is an integer from 0 to 3, preferably 0 or 1;
X is selected from (CH$_2$)$_n$, O, —(CH$_2$)$_q$NH—, or —(CH$_2$)$_q$N(CH$_3$)—, where n is an integer from 0 to 8 and q is an integer from 0 to 3, preferably 0 or 1;
Y is selected from (CH$_2$)$_m$, where m is an integer from 0 to 3; and
Z is selected from

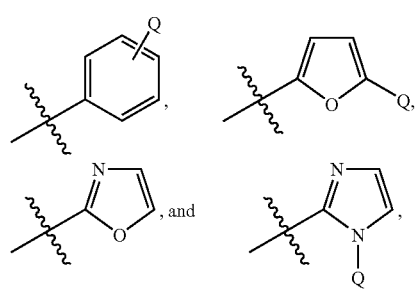

where Q is selected from H and halogen.
As used herein, the straight or branched chain hydrocarbons can be aliphatic or non-aliphatic, and includes both saturated hydrocarbons, monounsaturated hydrocarbons, and polyunsaturated hydrocarbons. Thus, this term is intended to include alkylene groups that contain a single carbon and up to a defined upper limit, as well as alkenyl groups and alkynyl groups that contain two carbons up to the upper limit, whether the carbons are present in a single chain or a branched chain.
As used herein, halogens can be any one of fluorine, chlorine, bromine, and iodine. Of these, fluorine and chlorine are preferred.
Preferred compound according to formula (I) include compounds A5 and A7 of Table 1.
Compounds of formula (I) having an ester group in the sidechain can be formed by standard esterification reactions between the appropriate isoquinoline carboxylic acid and an alcohol activated by reaction with, for example, dicyclohexyl carbodiimide. Accordingly, another aspect of the present invention relates to a method of making a compound of formula (I) where X is oxygen. This method involves providing an isoquinoline carboxylic acid according to formula (III)

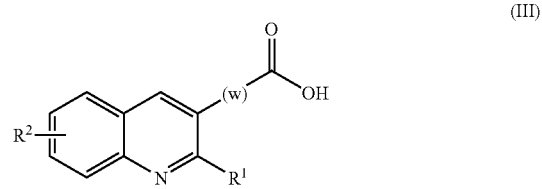

wherein R$^1$, R$^2$, and W are defined as in formula (I); and reacting the isoquinoline carboxylic acid of formula (III) with an alcohol of formula (IV)

HO-(y)-(z)          (IV), wherein Y and Z are defined as in formula (I). The reaction is carried out under conditions effective to make a compound according to formula (I) where X is oxygen.
Alternatively, compounds of formula (I) having an ester in the side chain (i.e., where X is O) can also be formed by using an acyl chloride according to formula (VI)

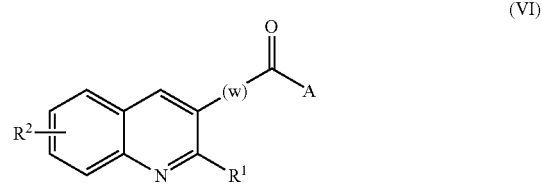

plus an alcohol according to formula (IV).

Compounds of formula (I) having a ketone group in the side chain (i.e., where X is $(CH_2)_n$) can also be formed. Accordingly, another aspect of the present invention relates to a method of making a compound of formula (I) where X is $(CH_2)_n$. This method involves providing an isoquinoline carboxylic acid according to formula (III) above. The isoquinoline carboxylic acid according to formula (III) is converted to a Weinreb amide via treatment with carbonyl diimidazole followed by N,O-Dimethylhydroxylamine according to the procedure of Nahm et al., *Tetrahedron Letters* 22:3815-3818 (1981), which is hereby incorporated by reference in its entirety. The resulting Weinreb amide is then treated with an alkyl Grignard reagent of formula (V)

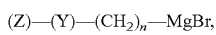 (V)

according to common procedures known by those of ordinary skill in the art, where Z and Y are defined as according to formula (I). These steps are carried out under conditions effective to make a compound of formula (I) where X is $(CH_2)_n$.

Compounds of formula (I) having an amide group in the sidechain can be formed by standard peptide coupling reactions in the manner described above.

By virtue of the activity of the furan compounds identified above in Table 1, the present invention also relates to compounds according to formula (II)

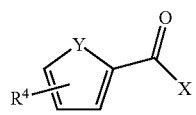 (II)

wherein,

R$^4$ is selected from H and straight or branched chain $C_1$ to $C_6$ hydrocarbon, preferably hydrogen, methyl, ethyl, or propyl;

Y is selected from O (e.g., furans), N—R$^5$ (e.g., pyrroles) and S—R$^5$ (e.g., thiophenes), where R$^5$ is selected from H and straight or branched chain $C_1$ to $C_6$ hydrocarbon, preferably hydrogen, methyl, ethyl, or propyl;

X is selected from R$^6$, O—R$^6$, NH—R$^6$, NR$^6_2$,

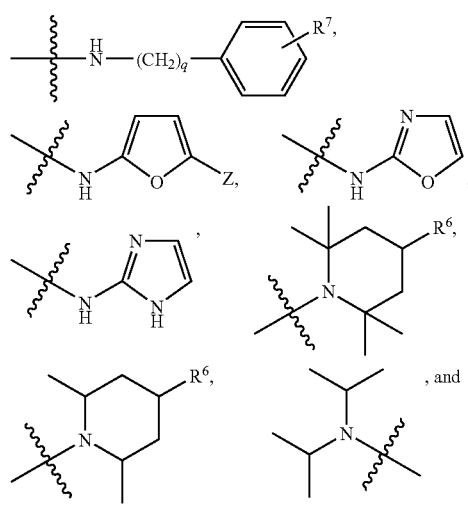

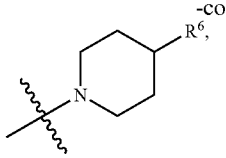

where each R$^6$ is independently selected from H, straight or branched chain $C_1$ to $C_6$ hydrocarbon, and halogen, preferably hydrogen, methyl, ethyl, propyl, fluorine, or chlorine; q is an integer from 0 to 5; and R$^7$ is selected from H, halogen, and $C_1$ to $C_3$ hydrocarbon, preferably hydrogen, fluoride, chlorine, methyl, ethyl, propyl, or isopropyl.

As used herein, the straight or branched chain hydrocarbons and halogens recited in formula (II) can be defined as above for formula (I). The same hydrocarbons and halogens are also preferred in this embodiment.

Preferred compounds according to this aspect of the present invention are compounds C1, C2, C5, C7, and C10 of Table 1.

Compounds of formula (II) having an amide group in the sidechain can be formed by standard peptide coupling reactions in the manner described above.

Compounds of formula (II) having an ester group in the sidechain can be formed by standard esterification reactions in the manner described herein.

Compounds of formula (II) having a ketone group in the sidechain can be formed by a standard ketone-forming reaction in the manner described herein.

The compounds of the present invention can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

As demonstrated in the examples, the compounds of the present invention have an ability to increase pigmentation in a cell (i.e., either directly in melanocytes or indirectly in keratinocytes). This method is carried out by providing a compound of the present invention, preferably though not exclusively those compounds identified in Table 1 or defined under formulae (I) and (II), and then contacting a cell with the compound under conditions effective to induce melanin expression in the cell, thereby increasing pigmentation.

Cells to be contacted in accordance with the present invention include any cells responsible for producing melanin, specifically melanocytes. Because the compounds of the present invention have the ability to induce melanin expression in melanocytes, and thereby increase melanin content of keratinocytes, it is intended for the compounds to be administered to skin in the form of an appropriate composition. The cells are preferably contacted in vivo after application of the composition to the skin of a subject, preferably a human subject.

The compositions of the present invention are preferably formulated to be administered by topical application to the skin (i e, keratinous tissue). Accordingly, the composition preferably has good aesthetic properties and will not cause any safety or toxicity concerns.

The carrier used in this and other compositions of the present invention can be in a wide variety of forms, including emulsion carriers, such as oil-in-water, water-in-oil, and oil-in-water-in-silicone emulsions, creams, ointments, ophthalmic ointments, aqueous solution, lotions, gels, or aerosols. As will be understood by the skilled artisan, a given component will distribute primarily into either the water or oil/silicone phase, depending upon the water solubility/dispersibility of the component in question. A safe and effective amount of carrier is from about 50% to about 99.99%, preferably from about 80% to about 99.99%, more preferably from about 90% to about 98%, and most preferably from about 90% to about 95% of the composition.

Emulsions generally contain an effective amount of a compound of the present invention and a lipid or oil. Lipids and oils may be derived from animals, plants, or petroleum, and can be natural or synthetic. Preferred emulsions also contain a humectant such as glycerin. Emulsions will preferably further contain from about 1% to about 10%, more preferably from about 2% to about 5%, of an emulsifier, based on the weight of the carriers. Emulsifiers may be ionic, anionic, or cationic. The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending upon the product form. Exemplary low viscosity emulsions, which are preferred, have a viscosity of about 50 centistokes or less, more preferably about 10 centistokes or less, most preferably about 5 centistokes or less. The emulsion may also contain anti-foaming agents to minimize foaming upon application to the skin.

Other preferred carriers include oil-in-water emulsions having a continuous aqueous phase and a hydrophobic, water-insoluble phase dispersed therein. Preferred oil-in-water emulsions comprise from about 25% to about 98%, preferably from about 65% to about 95%, and more preferably from about 70% to about 90% water by weight of the carrier.

The hydrophobic phase is dispersed in the continuous aqueous phase. The hydrophobic phase may contain water insoluble or partially soluble materials such as are known in the art including, but not limited to, silicones. The compositions of the present invention include, but are not limited to, lotions and creams, and may comprise a dermatologically acceptable emollient. As used herein, "emollient" refers to a material useful for preventing or relieving dryness, as well as for protecting the skin. A wide variety of suitable emollients are known and may be used herein. Numerous examples of materials suitable for use as an emollient are provided in Sagarin, *Cosmetics, Science, and Technology* 2nd Edition Vol. 1, pp 3243 (1972), which is hereby incorporated by reference in its entirety. A preferred emollient is glycerin. Glycerin is preferably used in an amount of from about 0.001% to about 20%, more preferably from about 0.01% to about 10%, and most preferably from about 0.1% to about 5%.

Lotions and creams according to the present invention generally comprise a solution carrier system and one or more emollients. Lotions typically comprise from about 1% to about 20%, preferably from about 5% to about 20%, of emollient; from about 50% to about 90%, preferably from about 60% to about 80%, water; and an effective amount of a compound of the present invention.

Ointments of the present invention may comprise a simple carrier base of animal or vegetable oil or semi-solid water soluble carriers. Ointments may further comprise a thickening agent and/or an emollient. For example, an ointment may comprise from about 2% to about 20% of an emollient, about 0.1 to about 2% of a thickening agent, and an effective amount of a compound of the present invention. To enhance the percutaneous absorption of the active ingredients, one or more of a number of agents can be added to the topical formulations, including but not limited to, dimethylsulfoxide (DMSO), dimethylacetamide, dimethylformamde, surfactants, azone, alcohol, acetone, propylene glycol, and polyethylene glycol. In addition, physical methods can also be used to enhance transdermal penetration such as e.g., by iontophoresis or sonophoresis. Alternatively, or in addition, the composition may be delivered in liposomes.

Compositions according to the present invention may also include optional components, which should be suitable for application to keratinous tissue, i.e., when incorporated into the composition they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds of the present invention. The CTFA Cosmetic Ingredient Handbook, Second Edition (1992) (which is hereby incorporated by reference in its entirety), describes a wide variety of non-limiting cosmetic and pharmaceutical ingredients commonly used in the skin care industry, which are suitable for use in the compositions of the present invention. Examples of these ingredient classes include abrasives, absorbents, aesthetic components such as fragrances, pigments, colorings, essential oils, skin sensates, astringents (e.g., clove oil, menthol, camphor, eucalyptus oil, eugenol, menthyl lactate, hazel distillate), anti-acne agents, anti-caking agents, antifoaming agents, antimicrobial agents, antioxidants, binders, biological additives, buffering agents, bulking agents, chelating agents, chemical additives, colorants, cosmetic astringents cosmetic biocides, denaturants, drug astringents, external analgesics, film formers or materials such as polymers for aiding the film-forming properties and substantivity of the composition (e.g., copolymer of eicosene and vinyl pyrrolidone), opacifying agents, pH adjusters, propellants, reducing agents, sequestrants and/or healing agents (e.g., panthenol and derivatives such as ethyl panthenol), aloe vera, pantothenic acid and its derivatives, allantoin, and bisabolol), skin treating agents, thickeners, and vitamins and derivatives thereof.

The compounds of the present invention stimulate melanin production and can be used topically for darkening skin, or to produce a safe tan. Accordingly, another aspect of the present invention relates to a method of increasing skin pigmentation. This method involves applying a composition of the present invention to skin on a subject in a manner and quantity effective to induce melanin production in contacted skin cells, thereby increasing skin pigmentation within a treated area of the skin.

The compounds of the present invention are useful in treating skin conditions where insufficient skin pigmentation is produced, or where the subject, for cosmetic purposes, simply wishes to develop a "sunless tan" or to augment tanning induced by a limited exposure to sunlight or ultraviolet light. Unlike previously known indoor tanning compositions, the compounds of the present invention actually produce additional melanin in the skin, and thus protect the skin from ultraviolet radiation.

The appropriate dose regimen, the amount of each dose administered, and specific intervals between doses of the active compound will depend upon the particular active compound employed, the conditions of the patient being treated, and the nature and severity of the disorder or conditions being treated. Preferably, the active compound is administered in an amount and at an interval that results in the desired treatment of or improvement in the disorder or condition being treated.

As one skilled in the art will readily appreciate, the compounds of the present invention can be used alone or in combination with one another, as well as in combination with the other melanin stimulating compounds described below, and with any other pigment affecting compounds.

The compounds of the present invention can be administered by any means that results in contact of the active agent with its site of action in the body of a mammal. The compounds can be administered by any conventional means available for use in conjunction with pharmaceuticals, either as individual therapeutic agents or in a combination of therapeutic agents. Each can be administered alone, but is preferably administered with a carrier selected on the basis of the chosen route of administration and standard pharmaceutical practice.

The compositions of the present invention are also useful for cosmetic purposes. Cosmetic applications include the topical application of compositions containing one or more compounds that affect pigmentation to enhance or otherwise alter the visual appearance of skin or hair. Occurrences in the skin or hair of noticeable but undesired pigmentation can be treated using the methods of the present invention.

An effective dosage and treatment protocol can be determined by conventional means, starting with a low dose in laboratory animals, and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can extrapolate doses for efficacy and avoidance of toxicity to other species, including humans.

Any one or a number of endpoints can be used to determine when to stop treatment. For example, endpoints can be defined subjectively such as, for example, when the subject is simply "satisfied" with the results of the treatment. Alternatively, endpoints can be defined objectively. For example, the subject's skin or hair in the treated area can be compared to a color chart. Treatment is terminated when the color of the skin or hair in the treated area is similar in appearance to a color chart. Alternatively, the reflectance of the treated skin or hair can be measured, and treatment can be terminated when the treated skin or hair attains a specified reflectance. In another method, the amount of melanin in the skin or hair can be measured. Melanin content can be determined in any way known in the art, including by histological methods, with or without enhancement by stains for melanin.

Compositions of the present invention are preferably administered pursuant to this aspect of the present invention by topical application. For topical administration, the compounds of the present invention can be formulated as a foam or mousse, solution, gel, lotion, ointment, cream, suspension, paste, liniment, powder, tincture, aerosol, transdermal drug delivery system, or the like, in a pharmaceutically or cosmetically acceptable form by methods well known in the art. The composition can be in any variety of forms common in the pharmaceutical or domestic arts for topical application to animals or humans, including solutions lotions, sprays, creams, ointments, salves, gels, aerosols, etc., as set forth above. Preferred agents are those that are viscous enough to remain on the treated area, those that do not readily evaporate, and/or those that are easily removed by rinsing with water topically with the aid of soaps, cleansers, and/or shampoos. Actual methods for preparing topical formulations are known or apparent to those skilled in the art.

Although the formulations and compositions are preferably delivered topically, it is also contemplated that the compositions can be delivered by various transdermal drug delivery systems, such as transdermal patches as known in the art.

EXAMPLES

The examples below are intended to exemplify the practice of the present invention but are by no means intended to limit the scope thereof.

Example 1

Synthesis and Analysis of a Library of Small Molecules

A 75 member combinatorial library was synthesized by reacting acid chlorides of carboxylic acids A-E with amines 1-15 (FIG. 1) (Dothager et al., *J. Am. Chem. Soc.* 127:8686 (2005), which is hereby incorporated by reference in its entirety). Carboxylic acid and amine components used for synthesizing the library were selected based on the presence of individual substructures in other "biologically active" compounds. Briefly, acid chlorides of A-E (1 eq) were prepared by reacting oxalyl chloride (3 eq), DMF (0.01 eq) and A-E in dry $CH_2Cl_2$ for 18 hours. Solvent was then removed under reduced pressure. Triethylamine (1.05 eq) and acid chlorides were added to 1-15 (1.05 eq) in dry $CH_2Cl_2$. DMAP (0.05 eq) was then added resulting in vigorous evolution of gas, and reactions were stirred at RT for 36 hours. Crude reaction mixtures were passed through a plug of silica gel, eluted with 1:1 hexanes:ethyl acetate, and dried. RP-HPLC and ESI-MS confirmed all reactions yielded pure desired products in varying yields. The purified library members were diluted to 25 mM stocks in DMSO for screening. All compounds of the library were confirmed by HPLC and MS data.

Example 2

Melanin Induction by Small Molecules

Figure 2:
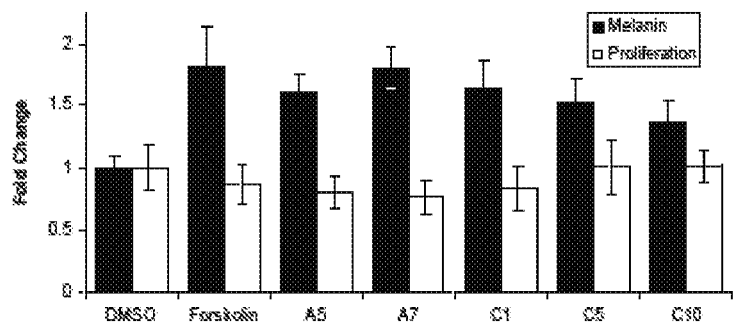
FIG. 2 is a graph showing melanin quantity and cell number (±S.D.) upon 2.5 µM small molecule treatment normalized to DMSO vehicle control.

The melan-a murine melanocyte cell line was chosen for library screening. This is a non-tumorogenic line of melanocytes derived from the skin of C57Bl/6J mice (Bennett et al., *Int. J. Cancer* 39:414 (1987), which is hereby incorporated by reference in its entirety). These cells are ideal for phenotypic melanin screening as they proliferate quickly, are highly differentiated, and have been extensively studied (Snyder et al., *Chemistry & Biology* 12(4):477 (2005), which is hereby incorporated by reference in its entirety). Melanocytes were cultured in RPMI 1640 media supplemented with 10% FBS and 0.2 µM TPA, at 37° C. under 5% $CO_2$, 95% atmosphere. For screening, $1 \times 10^5$ melan-a melanocytes were plated in 24 well tissue culture plates in a volume of 2 ml. After 18 hr incubation, 1 ml of media was removed and replaced by 1 ml media doped with small molecule, forskolin positive control, or DMSO vehicle control for 3 days. Initial screening was performed at a 2.5 µM dose (0.01% DMSO). Cells were harvested by trypsinization, washed 2× with PBS (pH 7.2), and counted by hemocytometry. Cell counts were used to assess treatment effects on cell proliferation. Melanin production was quantified by lysing cell pellets in 800 µl of 1 M NaOH for 2 hrs on ice, vigorously resuspending the lysed material by pipette, reading the absorbance at 490 nm of 200 μl aliquots of total lysate, and referencing to a standard synthetic melanin (Sigma) curve. The 75 member library was screened in triplicate. Melanin production was normalized to cell count ($A_{490}$/million cells) and fold change against DMSO was calculated (FIG. 2).

Figure 3:
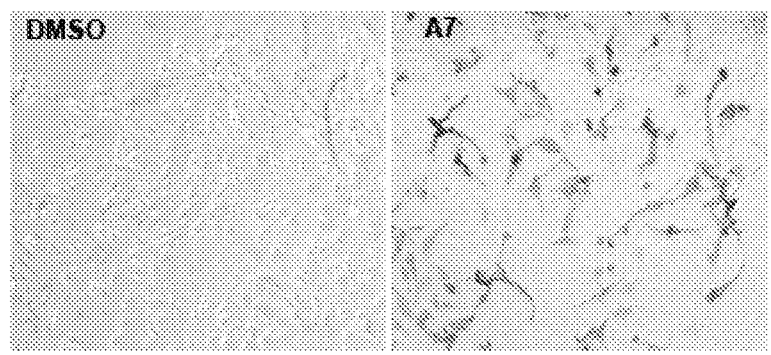
FIG. 3 is a pair of brightfield images of melan-a melanocytes cultured in the presence and absence of 2.5 µM of compound A7.
Figure 4:
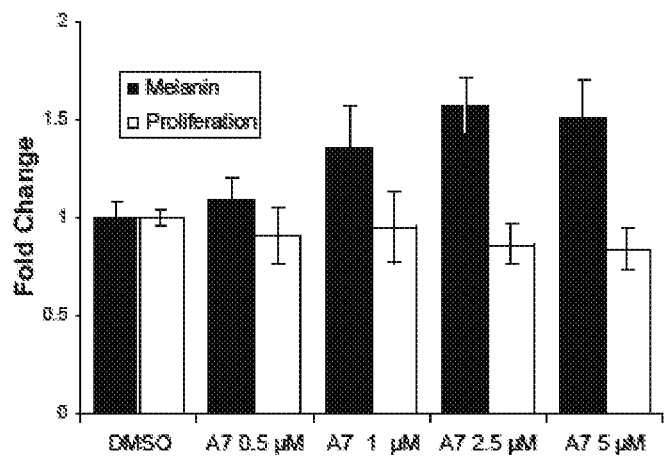
FIG. 4 is a graph showing dose response of melanin quantity and cell number (±S.D.) upon A7 treatment normalized to DMSO vehicle control.

Ten compounds from the library initially showed some activity for inducing melanin production. These included compounds A5, A7, C1, C2, C5, C7, C10, D10, D12, and E4 (see Table 1 above). Five library members significantly induced (greater than 40% increase) visible melanin production (FIG. 3) with similar potency to forskolin (FIG. 2). Importantly, the selected compounds did not affect cellular proliferation. Interestingly, there is a preference for fluorinated aromatic substituents. Importantly, compounds A5, A7, and C7, which contain the fluorinated aromatic substituents, were previously unknown. Subsequent analysis identified compound A7 as the most active hit, and studies were performed to further characterize its activity. First, A7 dose response was investigated (FIG. 4). Treatment with 2.5 μM A7 provided the optimal melanogenic response. Importantly, there was no significant effect on cell proliferation at concentrations up to 5 μM.

Example 3

Influence of Compound A7 on Melanocyte Dendricity

Figure 5:
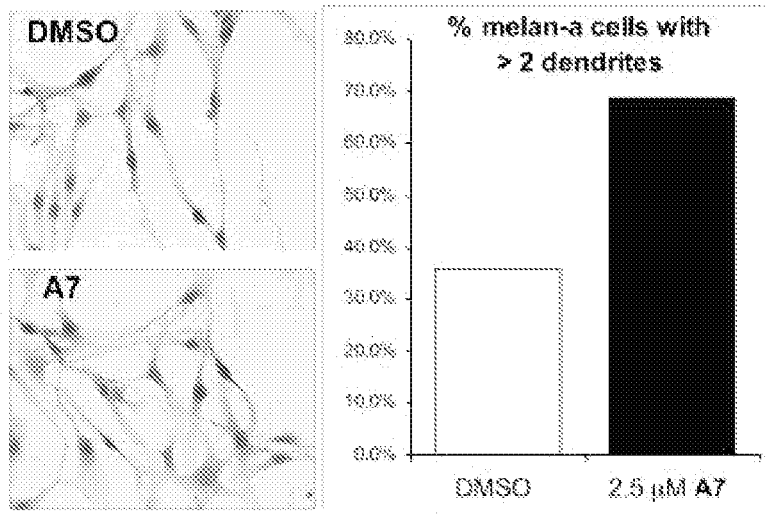
FIG. 5 shows images and a graph of hematoxylin stained melan-a melanocytes cultured in the presence and absence of 2.5 µM of compound A7.

In addition to melanin production, A7 treatment induced changes in cell morphology. Melanocytes are highly dendritic cells, and dendricity has been correlated with melanin production (Kosano et al., *Biochim. Biophys. Acta* 1499:11 (2000); Scott et al., *J. Invest. Dermatol.* 126:855 (2006), which are hereby incorporated by reference in their entirety). Dendricity was assessed by histochemical hematoxylin staining of melan-a melanocytes with and without 2.5 μM A7 treatment. $1 \times 10^4$ melan-a melanocytes were cultured onto vitrogen coated cover slips and treated with 2.5 μM A7 or vehicle control for 72 hours. Cells were fixed in 3.7% formalin/PBS, stained with hematoxylin, and imaged. Dendrites per cell were manually quantitated, and the percentage of cells with greater than 2 dendrites was calculated. As seen in FIG. 5, A7 treatment increases dendricity in addition to melanin formation: 36% of untreated and 69% of A7 treated melan-a melanocytes had greater than 2 dendrites.

Example 4

Influence of Compound A7 on Tyrosinase Activity

To further understand the mode of action for A7, tyrosinase activity was quantitated. Tyrosinase functions to hydroxylate tyrosine to dopaquinone and L-DOPA in the first step of melanin production (Ito, *Pigment Cell Res.* 16:230 (2003), which is hereby incorporated by reference in its entirety). As such, increased tyrosinase activity leads to increased melanin production. Tyrosinase activity can be measured by monitoring the production of tritiated water upon the hydroxylation of L-tyrosine-3,5-[$^3$H] to L-DOPA (Pomerantz, *J. Biol. Chem.* 241(1):161 (1966); Park et al., *J. Biol. Chem.* 268:11742 (1993), which are hereby incorporated by reference in their entirety).

Figure 6:
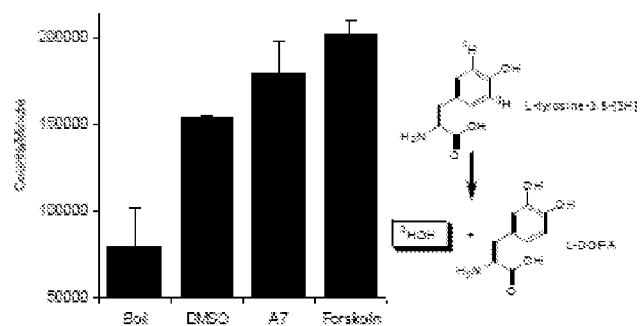
FIG. 6 is a graph showing tyrosinase assay (±S.D.) of melan-a melanocytes cultured in the presence and absence of 2.5 µM melanogenesis inducing small molecules.

Similarly to library screening, in quadruplet, melanocytes were cultured with and without 2.5 μM small molecule treatment for 3 days. Resulting cell pellets were lysed in 75 μl of 80 mM $K_2PO_4$, 1% CHAPS, 2 mM PMSF, and PICO2 protease inhibitor cocktail (CalBioChem) for 2 hours on ice. Lysates were then pelleted (10 minutes, 4° C., 10,000 rpm) and protein concentration was determined by Bradford assay. 2.5 μg aliquots of total protein were incubated in 250 μl of 80 mM $K_2PO_4$ containing 50 nM L-tyrosine, 25 nM L-DOPA, and 5 μCi of L-tyrosine-3,5-[$^3$H] for 60 minutes at 37° C. Proteins were precipitated (375 μl 0.2% BSA and 375 μl 10% TCA) and pelleted (10 minutes, 4° C., 10,000 rpm). 750 μl of the resulting supernatent was added to 500 μl of a 1:2 washed charcoal:80 mM $K_2PO_4$ suspension, nutated for 1 hour, and charcoal was pelleted (15 minutes, 4° C., 10,000 rpm). Aliqouts of 1.0 ml of the tritiated water containing supernatant were transferred to scintillation vials containing 5.0 ml scintillation fluid, and $^3$H levels were counted. Denatured protein samples of boiled aliquots served as negative controls, and forskolin served as a positive control. As seen in FIG. 6, A7 treatment increases tyrosinase activity in melanocyte culture, although to a lesser degree than forskolin treatment. Additionally, Western blot analysis suggests cellular levels of tyrosinase are not altered.

Example 5

Protein Analysis of Melanocytes Treated with Compound A7

Figure 7:
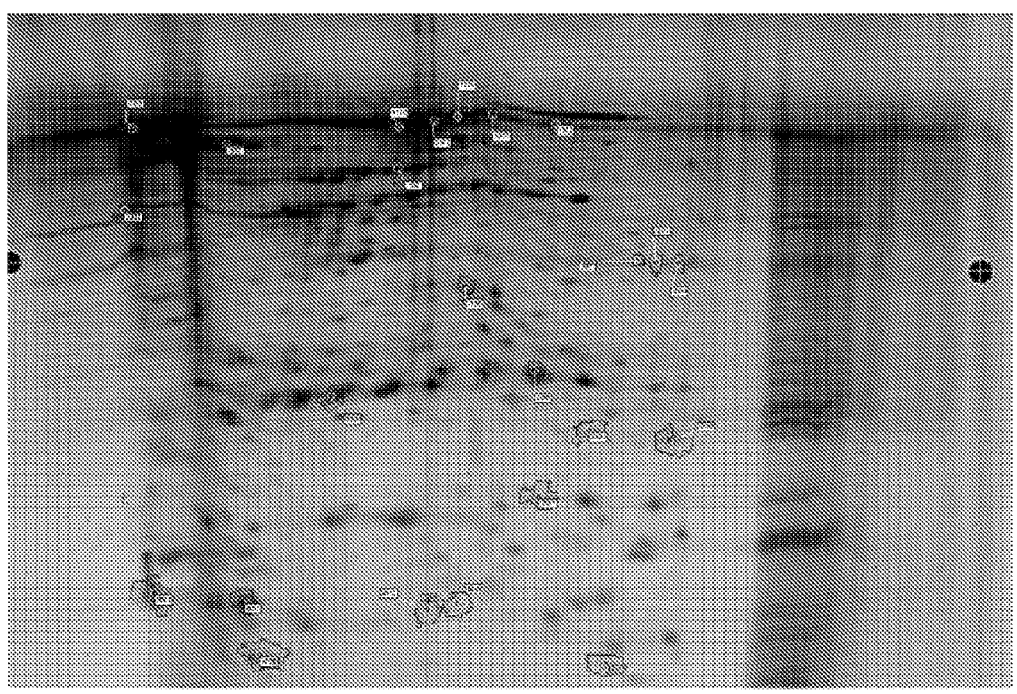
FIG. 7 is an image of a two-dimensional differential in gel electrophoresis. In total, 24 unique protein spots were reproducibly increased or decreased in two 2D-DIGE analyses upon treatment with A7 as compared to DMSO control.

To identify changes in specific protein amounts in the control versus A7 treated cells, two dimensional, differential gel electrophoresis was employed. In total, 24 unique protein spots were reproducibly increased or decreased in two 2D-DIGE analyses upon treatment with A7 as compared to DMSO control (FIG. 7). These proteins are in the process of being identified by MALDI-ToF mass spectrometry.

Discussion of Examples 1-5

In summary, phenotypic screening of a focused 75 member combinatorial library was used to identify a number of novel small molecules capable of inducing melanogenesis in melanocytes in culture. Of these, compound A7 proved to produce the best results. A7 has similar potency to the known melanogenic inducing agent forskolin, and does not exhibit cytotoxic effects in cell culture. In addition to melanin formation, A7 treatment results in increased cellular dendricity and tyrosinase activity, processes commonly associated with increased pigmentation. This novel compound represents a new class of melanogenesis inducing small molecules, structurally distinct from other compounds with similar function.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A composition comprising a compound according to formula (I)

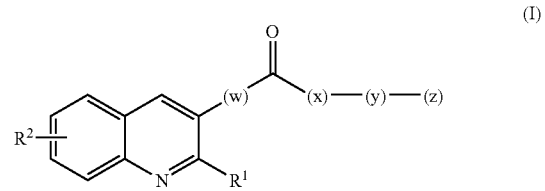

wherein
R¹ is selected from straight or branched chain $C_1$ to $C_6$ hydrocarbon;

R² is selected from H, —O—R³, —NH—R³, and —S—R³, where R³ is selected from H, straight or branched chain $C_1$ to $C_6$ hydrocarbon, and alkoxyalkyl;

W is optional and can be a straight or branched chain $C_1$ to $C_6$ hydrocarbon, —(CH$_2$)$_p$NH—, or —(CH$_2$)$_p$N(CH$_3$)—, where p is an integer from 0 to 3;

X is selected from (CH$_2$)$_n$, O, —(CH$_2$)$_q$NH—, or —(CH$_2$)$_q$N(CH$_3$)—, where n is an integer from 0 to 8 and q is an integer from 0 to 3;

Y is selected from (CH$_2$)$_m$—, where m is an integer from 0 to 3; and

Z is selected from

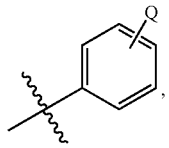 , 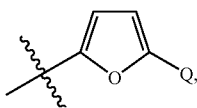

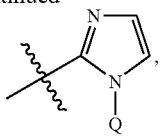 , and 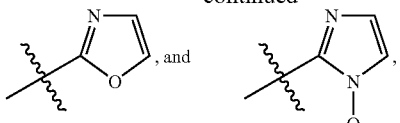

where Q is selected from H and halogen,
and a carrier, wherein the composition is in the form of a sunless tanning lotion.

2. A compound selected from the group of N-(4-fluorophenethyl)-2-ethylquinoline-3-carboxamide and N-(3-fluorophenethyl)-2-ethylquinoline-3-carboxamide.

3. The compound according to claim 2, wherein the compound is N-(4-fluorophenethyl)-2-ethylquinoline-3-carboxamide.

4. The compound according to claim 2, wherein the compound is N-(3-fluorophenethyl)-2-ethylquinoline-3-carboxamide.

5. A composition comprising a compound according to claim 2 and a carrier.

6. The composition according to claim 5, wherein the carrier is selected from the group of lotion, gel, solution, or aerosol.

* * * * *